United States Patent [19]

Tanaka et al.

[11] Patent Number: 4,841,091

[45] Date of Patent: Jun. 20, 1989

[54] PROCESS FOR PRODUCING 16-SUBSTITUTED PROSTAGLANDIN ES.

[75] Inventors: Toshio Tanaka; Atsuo Hazato; Seizi Kurozumi, all of Tokyo; Masahiro Koga, Yamaguchi, all of Japan

[73] Assignee: Teijin Limited, Osaka, Japan

[21] Appl. No.: 913,889

[22] PCT Filed: Jan. 28, 1986

[86] PCT No.: PCT/JP86/00034

§ 371 Date: Sep. 29, 1986

§ 102(e) Date: Sep. 29, 1986

[87] PCT Pub. No.: WO86/04330

PCT Pub. Date: Jul. 31, 1986

[30] Foreign Application Priority Data

Jan. 29, 1985 [JP] Japan ................................. 60-13527
Oct. 29, 1985 [JP] Japan ................................ 60-240439

[51] Int. Cl.$^4$ ........................................... C07C 177/00
[52] U.S. Cl. .................................. 558/441; 560/121; 560/231; 562/503
[58] Field of Search ............... 560/121, 231; 562/503; 558/441

[56] References Cited

U.S. PATENT DOCUMENTS 4,237,307  12/1980  Wissner ................. 560/121

FOREIGN PATENT DOCUMENTS 79733   5/1983  European Pat. Off. ........... 560/121
163842  8/1985  Japan ................. 560/121

OTHER PUBLICATIONS

Supplementary European Search Report.

Primary Examiner—Robert Gerstl

Attorney, Agent, or Firm—Sughrue, Mion, Zinn, Macpeak & Seas

[57] ABSTRACT

A novel process for manufacturing 16-substituted $\Delta^7$-prostaglandin Es, which include compounds expressed by the following formula (I), their enanantiomers, or their mixtures of arbitray mixing ratio,

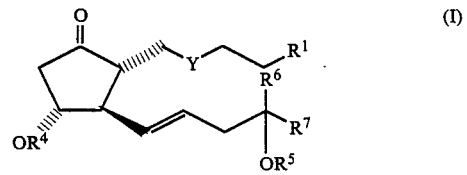

wherein $R^1$ indicates $COOR^2$; $CH_2OR^3$, in which $R^2$ indicates a hydrogen atom, a dubstituted or unsubstituted $C_1$–$C_{10}$ alkyl group, a substituted or unsubstituted $C_3$–$C_{10}$ cycloalkyl group, or a substituted or unsubstituted phenyl group, and $R^3$ indicates a hydrogen atom, a tri($C_1$–$C_7$) hydrocarbon silyl group, a group which forms an acetal bond together with the oxygen atom of a hydroxyl group, or a $C_2$–$C_7$ acyl group; $R^4$ and $R^5$ are identical or different, each representing a hydrogen atom, a tri($C_1$–$C_7$) hydrocarbon silyl group, or a group which forms an acetal bond together with the oxygen atom of a hydroxyl group; $R^6$ indicates a hydrogen atom, a $C_1$–$C_4$ alkyl group, or a vinyl group; $R^7$ indicates a linear or branched $C_3$–$C_8$ alkyl group, an alkyenyl group, or an alkynyl group, which may contain an oxygen atom; a phenyl group, a phenoxy group, or a $C_3$–$C_{10}$ cycloalkyl group, which may be substituted; or a linear or branched $C_1$–$C_5$ alkyl group which is substituted by a $C_1$–$C_6$ alkoxy group, a phenyl group a phenoxy group, or a $C_3$–$C_{10}$ cycloalkyl group, which may be substituted; and Y indicates $CH_2X$ or $XCH_2$, in which X represents an ethylene group, a cis -or trans-vinylene group, or an ethynylene group.

1 Claim, No Drawings

PROCESS FOR PRODUCING 16-SUBSTITUTED PROSTAGLANDIN ES.

FIELD OF THE INVENTION

The present invention relates to a novel process for producing 16-substituted prostaglandin Es. More particularly, this invention relates to a novel process for producing 16-substituted prostaglandin Es comprising allowing 4-substituted-2-cyclopentenones to react with an organocopper compound by means of conjugate addition to produce enolate intermediates, which intermediates are then allowed to react with aldehydes to give 7-hydroxy-16-substituted prostaglandin Es, which are thereafter converted into 7-organic sulfonyloxy-16-substituted prostaglandin Es and further into 16-substituted $\Delta^7$-prostaglandin Es and finally into originally desired 16-substituted prostaglandin Es.

BACKGROUND OF THE ART

Naturally occurring prostaglandins (abbreviated to PG) are known as local hormones (autacoid) which have high activities from the viewpoints of biology and pharmacology. Researches have, therefore, been made to develop medicines of a new type along the lines of not only naturally occurring PG but also their derivatives of various kinds by skillfully taking advantage of the physiological characteristic features of PGs.

Of the natural PGs, PGEs are the earliest known compounds, and $PGE_2$ has already been made into a drug to be used as an oxytocics because of its contractility on the smooth muscle of the uterus and $PGE_1$ is used as a therapeutic drug for peripheral circulatory disorders because of its physiological activities such as suppressive effect against the platelet aggregation and antihypertensive action.

With regard to the production of these PGEs, many processes have hitherto been developed and reported, and the following will be mentioned as epochal ones to represent these processes.

(i) A process for biosynthetically producing PGE from arachidonic acid or dihomo-γ-linolenic acid (see B. Samuelsson et al., Angew. Chem. Int. Ed. Engl., 4, 410 (1965)).

(ii) A process for obtaining PGE through an important intermediate Corey lactone (see E. J. Corey et al., J. Am. Chem. Soc., 92, 397 (1970)).

(iii) A process for producing PGE through an important intermediate 2-substituted-2-cyclopentenone compound (see C. J. Sih et al., J. Am. Chem. Soc., 97, 865 (1975)).

(iv) A process wherein 5,6-dehydro $PGE_2$ or $PGF_{2\alpha}$ is selectively reduced (see E. S. Ferdinandi et al., Can. J. Chem., 49, 1070 (1971); C. H. Lin et al., Prostaglandin, 11, 377 (1976)).

Of these methods mentioned above, the process for obtaining PGE by the biosynthetic method involves problems of difficulty in obtaining the material polyunsaturated fatty acid, very low yield from the material, and difficult isolation and purification from the by-product. While the process carried out according to chemical synthesis requires many steps of procedure before the starting material is obtained, and even when the starting material is made readily available, the process from the starting material to prostaglandin still includes many steps of procedure, thus lowering the total yield remarkably.

A report has been made with regard to a chemically synthetic process for producing PGEs based on the improvements made upon the aforementioned processes, including (i) the use of starting materials which are readily obtainable; (ii) the reaction process is short; and (iii) the total yield is high. The intended PGEs are produced by selectively removing the hydroxy group at the 7-position from 7-hydroxy PGEs, which have been obtained in high yield from protected 4-hydroxy-2-cyclopentenone in a single stage reaction, followed by the conversion of the functional group if necessary (see Noyori et al., Tetrahedron Letters, 23, 4057 (1982) and Tetrahedron Letters, 23, 5563 (1982)).

In parallel with the research and development of processes suited for practical use in synthesizing prostaglandin skeletons, many reports have also been made about the progress of researches conducted on the new applications of synthetic prostaglandins to medicaments and a number of resultant medical preparations based on the synthesized prostaglandin analogues. There is accordingly a strong demand for the development of more efficient and practical methods for the synthesis of skeletons of prostaglandin derivatives which are now very useful as medicaments.

DISCLOSURE OF THE INVENTION

Paying active attention to the aforementioned background of the prior art, the present inventors have made an exhaustive study of the process for deriving the desired PGEs from the key compounds of 7-hydroxy-16-substituted prostaglandin Es which can be obtained by subjecting 16-substituted prostaglandin Es to the three-component coupling reaction in which the aforementioned aldehyde is used as an enolate trapping agent and have succeeded in the development of an efficient process for producing 16-substituted prostaglandin Es which are useful as medicine, thus achieving the present invention.

The present invention relates to a process for producing 16-substituted prostaglandin Es, which include compounds expressed by the following formula (I), or their enantiomers, or their mixtures of arbitrary mixing ratio,

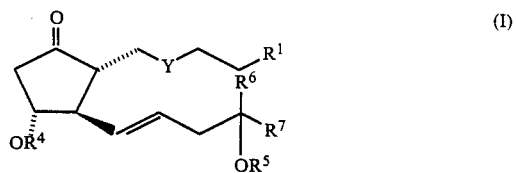

wherein $R^1$ indicates $COOR^2$, $CH_2OR^3$, or $COCH_2OR^3$, in which $R^2$ indicates a hydrogen atom, a substituted or unsubstituted $C_1$–$C_{10}$ alkyl group, a substituted or unsubstituted $C_3$–$C_{10}$ cycloalkyl group, or a substituted or unsubstituted phenyl group, and $R^3$ indicates a hydrogen atom, a tri ($C_1$–$C_7$) hydrocarbon silyl group, a group which forms an acetal bond together with the oxygen atom of a hydroxyl group, or a $C_2$–$C_7$ acyl group; $R^4$ and $R^5$ are identical or different, each representing a hydrogen atom, a tri ($C_1$–$C_7$) hydrocarbon silyl group, or a group which forms an acetal bond together with the oxygen atom of a hydroxyl group; $R^6$ indicates a hydrogen atom, a $C_1$–$C_4$ alkyl group, or a vinyl group; $R^7$ indicates a linear or branched $C_3$–$C_8$ alkyl group, an alkenyl group, or an alkynyl group, which may contain an oxygen atom; a phenyl group, a phenoxy group, or a $C_3$-$C_{10}$ cycloalkyl group, which may be substituted; or a linear or branched $C_1$-$C_5$ alkyl group which is substituted by a $C_1$-$C_6$ alkoxy group, a phenyl group, a phenoxy group, or a $C_3$-$C_{10}$ cycloalkyl group, which may be substituted; and Y indicates $CH_2X$ or $XCH_2$, in which X represents an ethylene group, a cis- or trans-vinylene group, or an ethynylene group, which process comprises making 7-hydroxy-16-substituted prostaglandin Es, which include compounds expressed by the following formula (IV'), their enantiomers, or their mixtures of arbitrary mixing ratio,

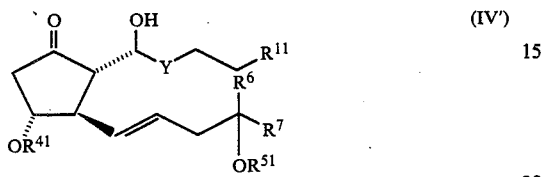

wherein $R^{11}$ indicates $COOR^{21}$, $CH_2OR^{31}$, or $COCH_2OR^{31}$, in which $R^{21}$ represents a substituted or unsubstituted $C_1$-$C_{10}$ alkyl group, a substituted or unsubstituted $C_3$-$C_{10}$ cycloalkyl group, or a substituted or unsubstituted phenyl group, and $R^{31}$ represents a tri($C_1$-$C_7$) hydrocarbon silyl group, a group which forms an acetal bond together with the oxygen atom of a hydroxyl group, or a $C_2$-$C_7$ acyl group; $R^{41}$ and $R^{51}$ are identical or different, each representing a tri ($C_1$-$C_7$) hydrocarbon silyl group, or a group which forms an acetal bond together with the oxygen atom of a hydroxyl group; $R^6$, $R^7$, and Y are as defined hereinbefore, to react with an organic sulfonic acid halide or anhydride in the presence of a basic compound to produce 7-organic sulfonyloxy-16-substituted prostaglandin Es, which include compounds expressed by the following formula (III'), their enantiomers, or their mixtures of arbitrary mixing ratio,

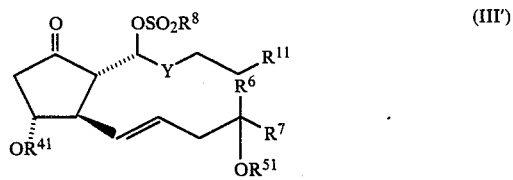

wherein $R^8$ indicates a $C_1$-$C_4$ alkyl group or a phenyl group which may be substituted; $R^{11}$, $R^{41}$, $R^{51}$, $R^6$, $R^7$, and Y are as defined hereinbefore, which are further treated with a basic compound, followed by the deprotecting reaction and/or the hydrolytic reaction, if necessary, to give 16-substituted $\Delta^7$-prostaglandin Es, which include compounds expressed by the following formula (II), their enantiomers, or their mixtures of arbitrary mixing ratio,

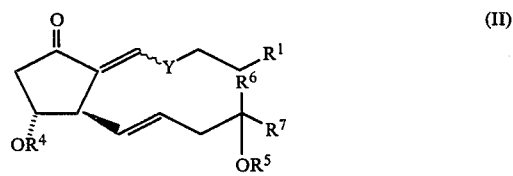

wherein $R^1$, $R^4$, $R^5$, $R^6$, $R^7$ and Y are as defined hereinbefore, and lastly selectively reducing the double bonds at the 7- and 8-positions, followed by the deprotecting reaction and/or the hydrolytic reaction, if necessary.

The 7-hydroxy-16-substituted prostaglandin Es of formula (IV'), which are the material compounds in the process for producing 16-substituted PGEs of the present invention, are produced as follows.

A 4-substituted-2-cyclopentenone (hereinafter referred to as a compound expressed by formula (VI')) represented by the following formula (VI')

wherein $R^{41}$ is as defined hereinbefore, is made to undergo the conjugate addition in the presence of a trivalent organic phosphorus compound with an organocopper compound, which is obtained from an organic lithium compound expressed by the following formula (VII')

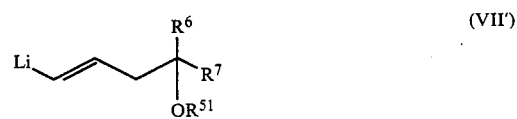

wherein $R^{51}$, $R^6$ and $R^7$ are as defined hereinbefore, and a copper compound expressed by the following formula (VIII)

wherein Q indicates a halogen atom, a cyano group, a phenylthio group, or a 1-pentynyl group, by the reaction carried out in an aprotic inert organic solvent, and then making the conjugate addition adduct react with an aldehyde expressed by the following formula (IX')

wherein $R^{11}$ and Y are as defined hereinbefore, to give the desired compound of formula (IV').

The abovementioned 4-substituted-2-cyclopentenone compounds expressed by formula (VI'), both their racemic form and optically active compounds, are all known compounds and can be easily obtained (Org. Syn. Chem., vol. 41, No. 10, pg. 896–903 (1983)). $R^{41}$ in the aforementioned formula (VI') and $R^{51}$ in the aforementioned formula (VII') are both hydroxyl-protecting groups and are identical or different, each representing a tri($C_1$-$C_7$) hydrocarbon silyl group, or a group which forms an acetal bond together with the oxygen atom of a hydroxyl group. As the tri($C_1$-$C_7$) hydrocarbon silyl group, such tri($C_1$-$C_4$) alkylsilyl groups as a trimethylsilyl group, triethylsilyl group, and t-butyldimethylsilyl group, and such diphenyl($C_1$-$C_4$) alkyl groups as a t-butyldiphenyl-silyl group, and such phenyldi($C_1$-$C_4$) alkyl groups as a phenyldimethylsilyl group or a tribenzylsilyl group may be mentioned. As the groups which form an acetal bond together with the oxygen atom of a hydroxyl group, a methoxymethyl group, 1-ethoxyethyl group, 2-methoxy-2-propyl group, 2-ethoxy-2propyl group, (2-methoxyethoxy) methyl group, benzyloxy methyl group, 2-tetrahydrofuranyl, and 6,6-dimethyl-3-oxa-2-oxobicyclo[3.1.0]-4-hexyl group, for instance, may be mentioned. Of these groups mentioned above, a trimethylsilyl group, t-butyldimethylsilyl group, diphenyl-t-butylsilyl group, 2-tetrahydrofuranyl group, 1-ethoxyethyl group, 2-ethoxy-2-propyl group, (2-methoxyethoxy) methyl group, and 6,6-dimethyl-3-oxa-2-oxobicyclo[3.1.0]-4-hexyl group may be mentioned as desirable ones for $R^{41}$ and $R^{51}$.

$R^6$ in the abovementioned formula (VII') indicates a hydrogen atom, $C_1$–$C_4$ alkyl group such as a methyl group, ethyl group, and butyl group, and a vinyl group, of which, a hydrogen atom, methyl group, and vinyl group may be mentioned as the desirable ones. $R^7$ indicates a linear or branched $C_3$–$C_8$ alkyl group, an alkenyl group, an alkynyl group, which may contain an oxygen atom; a phenyl group, a phenoxy group, a $C_3$–$C_{10}$ cycloalkyl group, which may be substituted; or a linear or branched $C_1$–$C_5$ alkyl group which is substituted by a $C_1$–$C_8$ alkoxy group, a phenyl group, a phenoxy group, a $C_3$–$C_{10}$ cycloalkyl group, which may be substituted. As the linear or branched $C_3$–$C_8$ alkyl group, alkenyl group, or alkynyl group, which may contain an oxygen atom; a 2-methoxyethyl group, 2-ethoxyethyl group, propyl group, butyl group, pentyl group, hexyl group, heptyl group, octyl group, 1-methyl-1-buthyl group, 2-methylhexyl group, 2-methyl-2-hexyl group, 2-hexyl group, 1,1-dimethylpentyl group, 1,5-dimethyl-4-hexenyl group, 1-butenyl group, 1-butynyl group, 2-butenyl group, and 2-butynyl group may be mentioned. Of these, a propyl group, butyl group, pentyl group, 1-methyl-1-butyl group, 2-methyl-1-butyl group, 1-butenyl group, 1-butynyl group, 2-butenyl group, and 2-butynyl group are preferable ones and a butyl group may be mentioned as an especially preferable one. As substituent of the phenyl group, phenoxy group, or $C_3$–$C_{10}$ cycloalkyl, which may be substituted; a halogen atom, hydroxy group, $C_2$–$C_7$ acyloxy group, $C_1$–$C_4$ alkyl group which may be substituted by a halogen atom, $C_1$–$C_4$ alkoxy group which may be substituted by a halogen atom, nitrile group, carboxyl group and ($C_1$–$C_6$) alkoxycarbonyl group are desirable ones. As the halogen atom, a fluorine atom, chlorine atom, and bromine atom may be mentioned and a fluorine atom and chlorine atom, are desirable. As the $C_2$–$C_7$ acyloxy group, an acetoxy group, propionyloxy group, n-butyryloxy group, isobutyryloxy group, n-valeryloxy group, isovaleryloxy group, caproyloxy group, enanthoyloxy group and benzoyloxy group may be mentioned.

As the $C_1$–$C_4$ alkyl group which may be substituted by a halogen atom, a methyl group, ethyl group, n-propyl group, isopropyl group, n-butyl group, chloromethyl group, dichloromethyl group, and trifluoromethyl group may be mentioned as preferable ones. As the $C_1$–$C_4$ alkoxy group which may be substituted by a halogen atom, a methoxy group, ethoxy group, n-propoxy group, isopropoxy group, n-butoxy group, chloromethoxy group, dichloromethoxy group and trifluoromethoxy group, for instance, may be preferable ones. As the $C_1$–$C_6$ alkoxycarbonyl group, an ethoxycarbonyl group, butoxycarbonyl group, and hexyloxycarbonyl group may be mentioned.

A substituted phenyl group, phenoxy group, or $C_3$–$C_{10}$ cycloalkyl group can have 1 to 3, preferably 1 of the aforementioned substituent groups. As the substituted or unsubstituted $C_3$–$C_{10}$ cycloalkyl group, such substituted by the same substituent groups as mentioned above or unsubstituted, saturated or unsaturated, groups of $C_3$–$C_{10}$, preferably $C_5$–$C_6$, or most preferably $C_6$, as a cyclopropyl group, cyclopentyl group, cyclohexyl group, cyclohexenyl group, cycloheptyl group, cyclooctyl group and cyclodecyl group, for instance, may be mentioned.

As linear or branched $C_1$–$C_5$ alkyl group which is substituted by the $C_1$–$C_6$ alkoxy group, phenyl group, phenoxy group, a $C_3$–$C_{10}$ cycloalkyl group, which may be substituted, those groups which are combinations of groups exemplified in the respective definitions given above may be mentioned as the preferable ones.

The carbon atom having substituents of $R^6$ and $R^7$ in the aforementioned formula (VII') is usually an asymmetric carbon atom with the configuration of either an R-isomer or an S-isomer, and the present invention involves both isomers, and furthermore involves dl-isomer and mixtures containing those of R- and S-isomer in an arbitrary mixing ratio.

In formula (VIII), Q indicates a halogen atom, a cyano group, a phenylthio group, or a 1-pentynyl group. As the halogen atom, a chlorine atom, bromine atom, and iodine atom may be mentioned. Of these, an iodine atom, cyano group, phenylthio group, and 1-pentynyl group are preferable and an iodine atom and 1-pentynyl group are especially preferable.

In formula (IX'), $R^{11}$ indicates $COOR^{21}$, $CH_2OR^{31}$, or $COCH_2OR^{31}$, in which $R^{21}$ represents a substituted or unsubstituted $C_1$–$C_{10}$ alkyl group, a substituted or unsubstituted $C_3$–$C_{10}$ cycloalkyl group, or a substituted or unsubstituted phenyl group, and $R^{31}$ indicates a tri($C_1$–$C_7$) hydrocarbon silyl group, a group which forms an acetal bond together with the oxygen atom of a hydroxyl group, or a $C_2$–$C_7$ acyl group.

As for $R^{21}$, those groups, which may be substituted by any of the substituent groups mentioned as the substituent groups in the aforementioned case of $R^7$, including linear or branched $C_1$–$C_{10}$ alkyl groups such as a methyl group, ethyl group, propyl group, isopropyl group, butyl group, sec-butyl group, isobutyl group, t-butyl group, pentyl group, hexyl group, heptyl group, octyl group, nonyl group, and decyl group, or $C_3$–$C_{10}$ cycloalkyl groups such as a cyclopropyl group, cyclopentyl group, cyclohexyl group, cyclooctyl group, and cyclodecyl group, or phenyl group may be mentioned. Of these mentioned above, $C_1$–$C_{10}$ alkyl groups, especially a methyl group is preferable.

As the tri($C_1$–$C_7$) hydrocarbon silyl group and the group which forms an acetal bond together with the oxygen atom of a hydroxyl group which are represented by $R^{31}$, these group which are cited for $R^{41}$ and $R^{51}$ may again be cited here as preferable ones, and as the $C_2$–$C_7$ acyl groups, those substituent groups exemplified for $R^7$ may be cited here again as desirable ones.

In formula (IX'), Y indicates $CH_2X$ or $XCH_2$, in which X represents an ethylene group, a cis- or trans-vinylene group, or an ethynylene group.

For obtaining an organocopper compound from an organic lithium compound expressed by formula (VII') and a copper compound expressed by formula (VIII), the literature, Tetrahedron; Lett., 21, 1247 (1980), may be suggested.

The reaction between 4-substituted-2-cyclopentenone expressed by formula (VI') and an organocopper compound is stoichiometrically conducted in equimolecular quantities; however, it is an ordinary practice to use 0.5 to 2.0 moles, most preferably 1.1 to 1.3 moles of an organocopper compound to 1 mole of 4-substituted-2-cyclopentenone.

The reaction temperature ranges from −120° C. to 0° C., most preferably from −90° C. to −30° C. The reaction time varies depending upon the reaction temperature; however, about 1 hour is ordinarily enough when the reaction is conducted at −78° C. to −20° C.

The reaction is carried out in the presence of an organic solvent. An inert aprotic organic solvent, which remains liquid at the reaction temperature and does not react with a reaction reagent, is to be used in the reaction.

As the inert aprotic organic solvent, such saturated hydrocarbons as pentane, hexane, and heptane; such aromatic hydrocarbons as benzene, toluene, and xylene; such etheric solvents as diethyl ether, tetrahydrofuran, dioxane, dimethyloxyethane, and diethylene glycol dimethyl ether; and ether so-called aprotic polar solvents such as hexamethylphosphonic triamide, N,N-dimethylformamide (DMAC), dimethyl sulfoxide, sulfolane, and N-methylpyrrolidone may be mentioned. These solvents can be used as a mixed solvent consisting of two or more solvents. As the aprotic inert organic solvent, the inert solvent which has been used in preparing said organocopper lithium compound can again be used in its entirety. This means that said 4-substituted-2-cyclopentenone is added to the reaction system in which said organic lithium compound has been prepared to cause the reaction. The amount of an organic solvent to be used in the reaction may be such as amount as enough to make the reaction proceed satisfactorily. It is an ordinary practice to use a solvent 1 to 100 times by volume, preferably 2 to 30 times by volume, the material.

It is advisable to carry out the reaction in an atmosphere of nitrogen or argon gas. It is better to carry on the reaction in the presence of trivalent phosphorus compound such as trialkylphosphine (like triethylphosphine and tributylphosphine), trialkylphosphate (like trimethyl phosphate, triethyl phosphate, and triisopropyl phosphate), etc. It is especially desirably to use tributylphosphine.

It is assumed in the present invention that all the operations taken up to this point have completed the formation of an enolate by conjugate addition to introduce an alkenyl group, which forms an organic radical of said organocopper compound, at the 3-position of the 4-substituted-2-cyclopentenone and resulted in the formation of an anion at the 2-position. When this enolate formed by conjugate addition is allowed to react with aldehyde expressed by the aforementioned formula (IX'), the desired 7-hydroxy-16 substituted prostaglandin E is obtained.

The reaction with said aldehyde is carried out by adding aldehyde of aforementioned formula (IX') which may be diluted with said aprotic organic solvent, to the reaction system in which an organocopper compound is conjugately added to the 4-substituted-2-cyclopentenone.

The reaction of said aldehyde with an enolate which has been prepared by conjugate addition proceeds stoichiometrically in amounts equimolar with each other; however, it is a usual practice to use 0.5 to 2.0 moles, or more preferably 0.8 to 1.2 moles of aldehyde to 1 mole of initially used 4-substituted-2-cyclopentenone.

The reaction is conducted at a temperature ranging from −120° C. to 0° C., preferably from −90° C. to −30° C. The reaction time varies depending upon the reaction temperature; however, the reaction is usually completed satisfactorily in about 1 hour at −78° C. to −40° C. It is efficient to determine the end point of the reaction by means of thin-layer chromatography and the like.

After the reaction is completed, the obtained product is isolated and purified from the reaction mixture according to the ordinarily practiced methods such as extraction, washing, chromatography, or their combination.

The product thus obtained has the structure represented by formula (IV') in which the respective hydroxyl groups and carboxylic acid are protected and is used as the starting material in the succeeding process.

The compound of formula (IV'), upon being subjected to the deprotecting reaction and/or the hydrolytic reaction as case may require, is led to 7-hydroxy-16-substituted prostaglandin Es expressed by the following formula (IV)

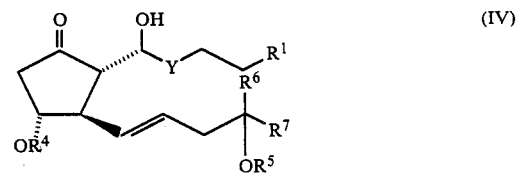

wherein $R^1$ indicates $COOR^2$, $CH_2OR^3$, or $COCH_2OR^3$, in which $R^2$ indicates a hydrogen atom, a substituted or unsubstituted $C_1$–$C_{10}$ alkyl group, a substituted or unsubstituted $C_3$–$C_{10}$ cycloalkyl group, or a substituted or unsubstituted phenyl group, and $R^5$ indicates a hydrogen atom, a tri($C_1$–$C_7$) hydrocarbon silyl group, a group which forms an acetal bond together with the oxygen atom of a hydroxyl group, or a $C_2$–$C_7$ acyl group; $R^4$ and $R^5$ are identical or different, each representing a hydrogen atom, a tri($C_1$–$C_7$) hydrocarbon silyl group, or a group which forms an acetal bond together with the oxygen atom of a hydroxyl group; $R^6$ indicates a hydrogen atom, a $C_1$–$C_4$ alkyl group, or a vinyl group; $R^7$ indicates a linear or branched $C_3$–$C_8$ alkyl group, an alkenyl group, or an alkynyl group, which may contain an oxygen atom; a phenyl group, a phenoxy group, or a $C_3$–$C_{10}$ cycloalkyl group, which may be substituted; or a linear or branched $C_1$–$C_5$ alkyl group which is substituted by a $C_1$–$C_6$ alkoxy group, a phenyl group, a phenoxy group, or a $C_3$–$C_{10}$ cycloalkyl group, which may be substituted; and Y indicates $CH_2X$ or $XCH_2$, in which X represents an ethylene group, a cis- or trans-vinylene group, or an ethynylene group, of which these derivatives whose $R^4$ and $R^5$ are both hydrogen atoms have per se physiological activities such as antiplatelet aggregation activity and anti-ulcer activity and form a group of compounds useful from the pharmaceutical viewpoint.

The deprotecting reaction, by which the hydroxyl-protecting groups ($R^{31}$, $R^{41}$, and/or $R^{51}$) in the compounds of formula (IV') are removed, is carried out successfully by use of acetic acid, pyridinium p-toluenesulfonate, or cation-exchange resin as a catalyst, and by use of water, tetrahydrofuran, ethyl ether, dioxane, acetone, or acetonitrile as a reaction catalyst, in case where the protecting group is a group which forms an acetal bond together with the oxygen atom of a hydroxyl group. The reaction is usually conducted at a temperature ranging from −78° C. to +30° C. for 10 minutes to 3 days. In case where the protecting group is a tri($C_1$-$C_7$) hydrocarbon silyl groups the reaction is carried out in the same solvent, at the same temperature, and for the same period of time as mentioned above, by use of acetic acid, tetrabutyl-ammonium fluoride, cesium fluoride, hydrofluoric acid, and hydrogen fluoride-pyridine as a catalyst.

The hydrolytic reaction for removing the carboxyl-protecting group ($R^{21}$) is conducted by use of such enzymes as lipase and esterase in water or water-containing solvent at a temperature ranging from $-10°$ C. to $+60°$ C. for 10 minutes to 24 hours.

In the process proposed by this invention, the 7-hydroxy-16-substituted prostaglandin Es of formula (IV') thus obtained are then made to react with an organic sulfonic acid halide or anhydride in the presence of a basic compound to be led to 7-organic sulfonyloxy-16-substituted prostaglandin Es represented by the following formula (III') (Process 1)

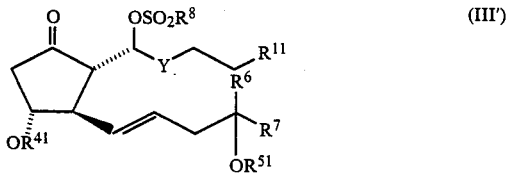

wherein $R^{11}$, $R^{41}$, $R^{51}$, $R^6$, $R^7$, $R^8$, and Y are as defined hereinbefore.

As the basic compound to be used here, amines are preferable ones and among them all, organic tertiary amines inclusive of heteroaromatic amines such as pyridine are especially preferable. As the organic tertiary amines, 4-dimethylaminopyridine, triethylamine, tributylamine, diisopropylethylamine, diisopropylcyclohexylamine, and isopropyldimethylamine, for instance, may be mentioned. Of these amines, the use of 4-dimethylaminopyridine, singly or in combination with any of other organic tertiary amines, is recommendable.

To give examples of the organic sulfonic acid halides, methanesulfonyl chloride, benzenesulfonyl chloride, and p-toluenesulfonyl chloride may be mentioned, and as the organic sulfonic acid anhydride, methanesulfonic acid anhydride may be mentioned.

The amount of organic sulfonic acid halide or anhydride to be used in the reaction ranges from 0.5 to 10 moles, preferably from 2 to 3 moles to 1 mole of 7-hydroxy-16-substituted prostaglandin Es expressed by formula (IV'), and the amount of the basic compound ranges from 1 to 20 moles, preferably from 2 to 5 moles likewise.

The reaction temperature ranges from $-20°$ C. to $50°$ C., preferably from $0°$ C. to $30°$ C. The completion of the reaction can be confirmed by following the disappearance of the material compound on thin-layer chromatography. The reaction is usually completed in 0.5 to 10 hours. A solvent may be used to make the reaction proceed smoothly. As the solvent to be used in the reaction, such halogenated hydrocarbons as dichloromethane, chloroform, and 1,2-dichloroethane, such ethers as ether, tetrahydrofuran, and dimethoxyethane, and such hydrocarbons as benzene, toluene, pentane, hexane, and cyclohexane may be mentioned. It is preferable to use dichloromethane. To mention the work-up after the reaction is over, the reaction product can be isolated and purified by subjecting the reaction mixture to the ordinary methods (such as extraction, washing, drying, chromatography, etc.).

The 7-organic sulfonyloxy-16-substituted prostaglandin Es expressed by formula (III') is isolated. Thus obtained compounds are not only useful as the intermediate in the succeeding stage of the present process but also useful substances per se as novel compounds.

$R^8$ in the aforementioned formula (III') represents a $C_1$-$C_4$ alkyl group or a phenyl groups which may be substituted. As the $C_1$-$C_4$ alkyl group, a methyl group, ethyl group, and butyl group may be mentioned, and of these groups, a methyl group is especially preferable. As the phehyl group which may be substituted, a phenyl group and p-toluyl group may be mentioned as preferable groups.

The 7-organic sulfonyloxy-16-substituted prostaglandin Es represented by the aforementioned formula (III') are then treated with a basic compound to be led to 16-substituted $\Delta^7$-prostaglandin Es expressed by the aforementioned formula (II') (Process 2).

As the basic compounds to be used here, the same basic compounds used in the proceeding Process 1 can also be used again. More particularly, the reaction of Process 1 shows up the very initial state of the reaction and when the treatment of the reaction mixture is continued for another long period of hours under the same conditions or under the raised reaction temperature, the reaction proceeds into Process 2, where the desulfonating reaction takes place as the secondary reaction, thus leading to the production of 16-substituted $\Delta^7$-prostaglandin Es represented by the following formula (II')

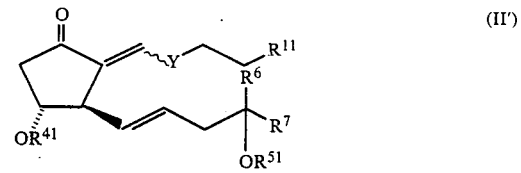

wherein $R^{11}$, $R^{41}$, $R^{51}$, $R^6$, $R^7$, and Y are as defined hereinbefore.

The 16-substituted $\Delta^7$-prostaglandin Es of formula (II') obtained in Process 1 and the succeeding work-up are further subjected to the deprotecting reaction and/or the hydrolytic reaction, if so required, to give 16-substituted $\Delta^7$-prostaglandin Es represented by the following formula (II)

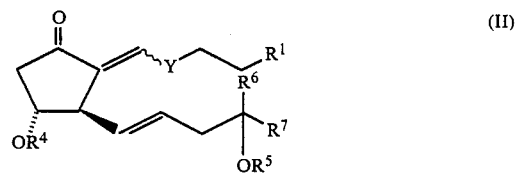

wherein $R^1$, $R^4$, $R^5$, $R^6$, $R^7$, and Y are as defined hereinbefore.

The group of these compounds are useful substances not only because they are used as the intermediates in the succeeding process but also because they function as the group of useful compounds which have per se the activities including activity of suppressing the proliferation of tumor cells, anti-platelet aggregation activity, and antiulcer activity, especially in case where said compounds have hydrogen atoms for $R^3$, $R^4$ and $R^5$ in their structures.

The 16-substituted Δ⁷-prostaglandin Es of formula (II) obtained in Process 2 are then have their double bonds at the 7- and 8-positions reduced selectively and further subjected to the deprotecting reaction and/or hydrolytic reaction, if so required, to be led to 16-substituted prostaglandin Es, or the final products of this invention, expressed by the following formula (I)

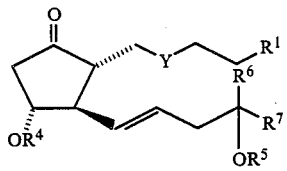

wherein $R^1$, $R^4$, $R^5$, $R^6$, $R^7$, and Y are as defined hereinbefore.

The reaction for selectively reducing the double bonds at the 7- and 8-positions can be achieved according to the following methods.

(i) The reduction reaction in which an organic tin hydride compound is used.

(ii) The reduction which is carried out by use of zincic reducing agents such as zinc dust, zinc-silver, and zinc-copper in the presence of acetic acid.

(iii) The catalytic reduction conducted in the presence of the catalyst for hydrogenation such as nickel, palladium, platinum, and rhodium.

These methods are explained in detail as follows.

(i) Reduction by use of organic tin hydride:

As the organic tin hydride to the used in this reduction reaction, dibutyltin dihydride, tripropyltin hydride, triethyltin hydride, tributyltin deuteride, and triphenyltin hydride, for instance, may be mentioned. Tributyltin hydride is especially preferable because of its easy availability.

The amount of an organic tin hydride compound varies depending upon its reactivity; however, it is a usual practice to use 1 to 1000 moles of organic tin hydride, more preferably 1 to 100 moles, and most preferably 2 to 10 moles, to 1 mole of the material compound of formula (II). A reaction solvent may be used as case may require. Benzene, tetrahydrofuran, chloroform, and dioxane are usually used; however, the reaction proceeds in the absence of a solvent and it is advisable not to use a solvent in a case where the reaction system is homogeneous.

The reaction is conducted in the presence of a reaction accelerator. As the reaction accelerator, such radical initiators as α, α'-azobisisobutyronitrile and di-t-butyl-peroxide, and zerovalent palladium catalyst are used favorably.

In case where a radical initiator is used as the reaction accelerator, it is usually used in an amount of 0.001 to 10 moles to 1 mole of the starting material of formula (II). The reaction temperature ranges from 0° C. to 200° C., preferably from 30° C. to 140° C.

As the zerovalent palladium catalyst, a zerovalent palladium itself or ones which form complexes with appropriate ligands may be mentioned; however, a zerovalent palladium complex which has the improves solubility for organic substances is preferable from the viewpoint of efficiency of a catalyst. As the ligands of such zerovalent palladium catalyst, 1,2-diphenylphosphine ethane, methyl-diphenylphosphine, triphenylphosphine, and dibenzylideneacetone may be mentioned, of which triphenylphosphine is especially preferable. As the zerovalent palladium complex coordinated with such a ligand, tetrakis (triphenylphosphine) palladium (0) may be mentioned.

Also, the reaction proceeds satisfactorily even if a zerovalent palladium catalyst is formed by reduction in the reaction system and this may be accepted willingly in this invention.

The amount of the zerovalent palladium catalyst to be used in the reation is relative to its efficiency as a catalyst; however, it is usually enough to use it in an amount of 0.001 to 10 moles, preferably 0.01 to 1 mole to 1 mole of the material compound of formula (II).

The reaction is conducted at a temperature ranging from 0° C. to 100° C., preferably from 20° C. to 60° C. The reaction is carried out in the range of 1 to 48 hours but the reaction temperature and time usually varies depending upon the catalyst and reductant. The reaction can be conducted efficiently while following its process by means of gas chromatography, liquid chromatography, thin-layer chromatorgraphy.

After the reaction is over, the 16-substituted prostaglandin Es represented by the abovementioned formula (I) are isolated and purified according to the ordinary methods, such as by addition of water, extraction, washing, drying, separation by filtration, and concentration, followed by separation by means of chromatography.

(ii) Reduction by use of zincic reducing agents in the presence of acetic acid:

As the zincic reducing agents to be used in the reaction, zinc dust, zinc-silver, and zinc-copper may be mentioned. The amount of a zincic reductant to be used in the reaction is 1 to 100 moles, preferably 2 to 50 moles, to 1 mole of the material compound of formula (II). A solvent is used to make the reaction proceed smoothly. As the solvents, alcohols such as methanol, ethanol, and butanol; acetic acid, dimethyl sulfoxide, or a mixture thereof are preferably used. Of these solvents, methanol is especially preferable.

The reaction temperature ranges from 0° C. to 120° C., preferably from 10° C. to 80° C. The reaction time, which varies depending upon the reaction conditions, should preferably in the range of 1 to 48 hours, more preferably 3 to 24 hours. After the reaction is completed, the reaction mixture is subjected to ordinary aftertreatments to isolate the 16-substituted prostaglandin Es expressed by the aforementioned formula (I).

(iii) Reaction by use of catalyst for hydrogenation:

As the catalysts for hydrogenation to be used in this reaction, which is conducted by used of heterogeneous catalysts for hydrogenation in the atmosphere of hydrogen, Raney nickel catalyst, palladium catalyst, platinum catalyst, and rhodium catalyst may be mentioned. The amount of the catalyst to be used in the reation ranges from 0.001 to 20 moles, preferably from 0.01 to 10 moles, to 1 mole of the material of formula (II).

A solvent is used to make the reaction proceed smoothly. As the solvent, such alcohols as methanol, ethanol, and butanol such ethers as dimethoxyethane, and tetrahydrofuran; dimethylformamide; or a mixed solvent thereof are preferably used. Methanol is used most preferably.

After the reduction reaction is over, the reaction product may further be subjected to the deprotecting reaction and/or hydrolytic reaction, if necessary.

The intermediates are thus made into the 16-substituted prostaglandin Es of formula (I), which are the final compound aimed at in the present invention, through Process 3.

The concrete examples of the 16-substituted prostaglandin Es expressed by formula (I) are as follows.
16-methyl-15-deoxy-16-hydroxy PGE$_1$
(16S)-16-methyl-15-deoxy-16-hydroxy PGE$_1$
(16R)-16-methyl-15-deoxy-16-hydroxy PGE$_1$
16-methyl-15-deoxy-16-hydroxy PGE$_2$
16-methyl-15-deoxy-16-hydroxy-5,6-dehydro PGE$_2$
16-vinyl-15-deoxy-16-hydroxy PGE$_1$
16-vinyl-15-deoxy-16-hydroxy PGE$_2$
(4Z)-15-deoxy-16-hydroxy-$\Delta^4$-PGE$_1$
(4E)-15-deoxy-16-hydroxy-$\Delta^4$-PGE$_1$
(16S, 4Z)-16-methyl-15-deoxy-16-hydroxy-$\Delta^4$-PGE$_1$
(16S, 4Z)-16-methyl-15-deoxy-16-hydroxy-$\Delta^4$-PGE$_1$
16-methyl-15-deoxy-16-hydroxy-4,4,5,5-tetradehydro PGE$_1$
(4Z)-16-vinyl-15-deoxy-16-hydroxy-$\Delta^4$-PGE$_1$
(4E)-16-vinyl-15-deoxy-16-hydroxy-$\Delta^4$-PGE$_1$ As fully described in the above, the present invention is to provide a new industrially advantageous process for producing 16-substituted prostaglandin Es and also provide 7-hydroxy-16-substituted prostaglandin Es and 16-substituted $\Delta^7$-prostaglandin Es which are important intermediates in said process of production and also make useful medicines per se because of their excellent pharmacological activities such as anti-ulcer activity and anti-platelet aggregation activity.

BEST MODE OF CARRYING OUT THE INVENTION

The best mode of carrying out the present invention is described in detail by the following examples.

EXAMPLE 1

Synthesis of (dl)-7-hydroxy-15-deoxy-16-methyl-11-t-butyldimethylsilyl-16-trimethylsilyloxy-PGE, methyl ester A flask was cooled at $-78°$ C. and 10 ml of anhydrous ethyl ether was put in the flask and then a 1.6M butyllithium solution (15 ml, 24 mM) was added thereto. Then, 10 ml of anhydrous ethyl ether solution of 3.91 g (11.5 mM) of (dl)-(E)-4-methyl-4-trimethylsilyloxy-1-iodo-1-octene which was cooled at $-78°$ C. was added to the mixture. The reaction mixture was stirred for 2 hours.

A homogeneous solution was separately prepared by stirring a mixture of 1.57 g (12 mM) of 1-pentynylcopper (I), 6.53 ml (36 mM) of hexamethylphosphorous triamide and 10 ml of anhydrous ethyl ether, for 30 minutes. The solution was cooled to $-78°$ C. and added to the abovementioned reaction mixture and stirred for 1 hour.

A $-78°$ C. solution of 2.12 g (10 mM) of (dl)-4-t-butyldimethylsilyloxy-2-cyclopentenone in 20 ml of anhydrous ethyl ether was added to the aforementioned reaction mixture. The mixture was stirred at $-78°$ C. for 10 minutes and was further stirred at $-40°$ C. for 40 minutes.

To the mixture, an ethereal solution (10 ml) of 1.90 g (12 mM) of methyl 7-oxo heptanoate was added at $-40°$ C. and the whole mixture was stirred at $-40°$ C. for 1 hour.

The reaction mixture was poured into an aqueous acetate buffer solution (pH 4) and stirred for 15 minutes. After it was filtered through Celite, it was washed with a small amount of n-hexane, and extracted. The separated organic layers were collected and washed with an aqueous solution of ammonium chloride and a saturated saline solution. After having been dried over anhydrous magnesium sulfate and concentrated under vacuum, a crude residue was subjected to chromatography over silica gel to give 2.94 g (yield 50%) of (dl)-7-hydroxy-15-deoxy-16-methyl-11-t-butyldimethylsilyl-16-trimethylsilyloxy-PGE, methyl ester.

Rf=0.54 (n-hexane: ethyl acetate=2:1).
IR (KBr-disk): 3450, 1740, 1250, 840 cm$^{-1}$,
$^1$H-NMR (CDCl$_3$, $\delta$): 0–0.2 (m, 15H), 0.75 (m, 12H), 1.15–1.55 (m, 18H), 2.0–2.5 (m, 8H), 3.1–3.2 (m, 1H), 3.50 (s, 3H), 3.8–4.1 (m, 1H), 5.1–5.5 (m, 2H).

EXAMPLE 2

Synthesis of (dl)-7,8-dehydro-15-deoxy-16-methyl-11-t-butyldimethylsilyl-16-trimethylsilyloxy-$^{PGE}$1 methyl ester One gram of (dl)-7-hydroxy-15-deoxy-16-methyl-11-t-butyldimethylsilyl-16-trimethylsilyloxy-PGE$_1$ methyl ester was dissolved in 7 ml of dichloromethane and then 1.04 g of 4-dimethylaminopyridine was added thereto. To the mixture, 0.29 ml of methanesulfonyl chloride was added at 0° C. and the resulting mixture was stirred for 10 minutes. Thereafter the mixture was stirred at 25° C. for additional 3 hours. The reaction mixture was poured into an aqueous solution of KHSO$_4$ and was extracted with dichloromethane. The separated organic layer was washed with a saturated aqueous solution of sodium hydrogencarbonate, then with a saturated saline solution, and was dried over anhydrous magnesium sulfate. The concentrated reaction product was then subjected to column chromatography over silica gel to provide 0.65 g (yield of 67%) of (dl)-7,8-dehydro-15-deoxy-16-methyl-11-t-butyldimethylsilyl-16-trimethylsilyloxy-PGE$_1$ methyl ester.

Rf=0.56 (n-hexane: ethyl acetate=3:1),
IR (liquid film): 1735, 1730, 1250, 840 cm$^{-1}$,
$^1$H-NMR (CDCl$_3$, $\delta$): 0–0.2 (m, 15H), 0.8 (m, 12H), 1.1–1.75 (m, 15H), 2.0–2.5 (m, 8H), 3.3–3.4 (m, 1H), 3.65 (s, 3H), 4.0–4.2 (m, 1H), 5.2–5.4 (m, 2H), 6.4–7.0 (m, 1H).

EXAMPLE 3

Synthesis of (dl)-15-deoxy-16-methyl-11-t-butyldimethylsilyloxy-16-trimethylsilyl-$^{PGE}$1 methyl ester One hundred and eighty milligrams of (dl)-7,8-dehydro-15-deoxy-16-methyl-11-t-butyldimethylsilyl-16-trimethylsilyloxy-PGE$_1$ methyl ester obtained in Example 2 was dissolved in 5 ml of isopropyl alcohol and 0.4 ml of acetic acid and further 400 mg of zinc dust were added to the solution. The mixture was stirred at 60° C. for 1 hour. After having been cooled, the reaction mixture was filtered through Celite, and washed with ethyl acetate. The filtrate was washed with a saturated saline solution, dried over anhydrous magnesium sulfate, filtered, concentrated in vacuo, and subjected to column chromatography over silica gel to obtain 118 mg (yield of 66%) of (dl)-15-deoxy-16-methyl-11-t-butyldimethylsilyloxy-16-trimethylsilyl-PGE$_1$ methyl ester.

IR (liquid film): 1740.
$^1$H-NMR (CDCl$_3$, $\delta$): 0–1.0 (m, 15H), 0.85 (s+t, 12H), 1.15 (s, 3H), 1.1–1.75 (m, 16H), 2.0–2.6 (m, 8H), 3.6 (s, 3H), 3.8–4.1 (m, 1H), 5.2–5.5 (m, 2H).
Rf=0.52 (n-hexane: ethyl acetate=4:1).

EXAMPLE 4

Synthesis of (dl)-15-deoxy-16-methyl-11-t-butyldimethylsilyloxy-16-trimethylsilyl-$^{PGE}$1 methyl ester A mixture of 100 mg of (dl)-7,8-dehydro-15-deoxy-16-methyl-11-t-butyldimethylsilyl-16-trimethylsilyloxy-$PGE_1$ methyl ester, 200 mg of tetrakis (triphenylphosphine) palladium catalyst, and 0.2 ml of n-tributyltin hydride was stirred at room temperature for 12 hours. Thereafter, a saturated aqueous solution of ammonium chloride was added to the reaction mixture, then extracted with n-hexane, and the organic layer was washed with a saturated saline solution. After the organic layer was dried over anhydrous magnesium sulfate and evaporated, an obtained residue was subjected to column chromatography over silica gel to give 55 mg (yield of 55%) of (dl)-15-deoxy-16-methy-11-t-butyldimethylsilyl-16-trimethylsilyloxy-$PGE_1$ methyl ester, the same compound as the one obtained in Example 3.

EXAMPLE 5

Synthesis of (dl)-15-deoxy-16-hydroxy-16-methyl prostaglandin $^E$1 methyl ester To solution of (dl)-(16RS)-11-t-butyldimethylsilyl-15-deoxy-16-methyl-16-trimethylsilyloxy prostaglandin $E_1$ methyl ester (537 mg, 0.95 m mol) in acetonitril (15 ml) was put in a 50-ml reaction vessel, and pyridine (0.6 ml), then hydrogen fluoride-pyridine complex (0.6 ml) were added. The mixture was stirred at room temperature for 2.5 hours. The reaction was monitored by thin layer chromatography. After the reaction was completed, the reaction mixture was neutralized by addition of saturated aqueous solution of sodium hydrogen-carbonate and the resulting mixture was extracted with ethyl acetate. After the extract was washed with an aqueous solution of potassium hydrogen sulfate, with an aqueous solution of sodium hydrogencarbonate, and with a saline solution, the separated organic layer was dried over anhydrous magnesium sulfate and concentrated to leave a crude product. The crude product was subjected to column chromatography (30 g of silica gel; hexane: ethyl acetate=1:2) to afford (dl)-15-deoxy-16-hydroxy-16-methylprostaglandin $E_1$ methyl ester (310 mg, 0.82 m mol, yield 86%).

IR (liquid film): 3410, 1740, 1160, 970, 730 cm$^{-1}$.

$^1$H-NMR (CDCl$_3$, δ): 0.87 (3H, t), 1.13 (3H, s), 1.1–1.8 (16H, m), 2.0–3.0 (8H, m), 3.63 (3H, s) 3.7–4.3 (1H, m), 5.1–5.9 (2H, m).

EXAMPLE 6

Synthesis of (dl)-(4Z)-7-hydroxy-15-deoxy-16-methyl-11-t-buthyl-dimethylsilyl-16-trimethylsilyloxy-$\Delta^4$-$^{PGE}$1 methyl ester An anhydrous ether (10 ml) solution of (dl)-(E)-4-methyl-4-trimethylsilyloxy-1-iodo-1-octene (1.12 g, 3.3 m mol) was cooled to −78° C. and 2.0M t-butyllithium (3.3 ml, 6.6 m mol) was added thereto. The mixture was stirred at −78° C. for 2 hours. Separately, 5 ml of anhydrous ether and then 1.08 g (6.6 m mol) of hexamethylphosphorous triamide were added to 431 mg (3.3 m mol) of 1-pentynylcopper (I) and the mixture was stirred at room temperature for 30 minutes to make a homogeneous solution. The solution was then added to the aforementioned reaction mixture and the resultant mixture was stirred at −78° C. for 1 hour.

Next, an anhydrous tetrahydrofuran solution (5 ml) of (dl)-4-t-butyldimethylsilyloxy-2-cyclopentenone (616 mg, 3.0 m mol) was added to the mixture at −78° C. and stirred at −78° C. for 10 minutes and then at −40° C. for 1 hour. Furthermore, an anhydrous ether solution (5 ml) of methyl (4Z)-6-formyl-4-hexenoate (515 mg, 3.3 m mol) was added thereto and was stirred at −40° C. for 1 hour.

The reaction mixture was then poured into 2.0 M acetate buffer solution and 100 ml of hexane was further added thereto and stirred. The whole mixture was filtered through Celite. The filtrate was washed two times with an aqueous solution of ammonium chloride containing ammonia, then with an aqueous solution of ammonium chloride, and lastly with a saline solution. The separated organic layer was then dried over anhydrous magnesium sulfate and concentrated under vacuum to give a crude product. This crude product was subjected to column chromatography on silica gel (hexane: ethyl acetate=9:1) to obtain the desired (dl)-(4Z)-7-hydroxy-15-deoxy-16-methyl-11-t-butyldimethylsilyl-16-trimethylsilyloxy-$\Delta^4$-$PGE_1$ methyl ester (1.17 g, 2.0 m mol, yield 67%).

Rf=0.35 (hexane: ethyl acetate=4:1), $^1$H-NMR (δppm in CDCl$_3$): 0.06 (6H, s), 0.10 (9H, s), 0.90 (12H), 1.16 (3H, s), 1.2–1.5 (6H, m), 3.2–3.4 (1H, m), 3.73 (3H, s), 3.7–4.4 (2H, m), 5.15–6.10 (4H, m).

IR (neat): 3500, 3000, 1740, 1255, 1245, 1150, 1110, 1095, 1050, 1000, 970, 885, 835, 775, 745 cm$^{-1}$.

EXAMPLE 7

Synthesis of (dl)-(4Z)-7,8-dehydro-15-deoxy-16-methyl-11-t-butyl-dimethylsilyl-16-trimethylsilyloxy-$\Delta^4$-$^{PGE}$1 methyl ester The reaction of (dl)-(4Z)-7-hydroxy-15-deoxy-16-methyl-11-t-butyldimethylsilyloxy-16-trimethylsilyloxy-$\Delta^4$-$PGE_1$ methyl ester (1.17 g, 2.0 m mol) obtained in Example 6 with methanesulfonyl chloride (298 mg, 2.6 m mol) was carried out in the presence of 4-dimethylaminopyridine (732 mg, 6.0 m mol) according to Example 2. The reaction product was subjected to the same work-up and purification by column chromatography as Example 2 to provide (dl)-(4Z)-7,8-dehydro-15-deoxy-16-methyl-11-t-butyldimethylsilyl-16-trimethylsilyloxy-$\Delta^4$-$PGE_1$ methyl ester (875 g, 1.52 m mol, yield 76%).

Rf=0.55 and 0.50 (hexane: ethyl acetate=4:1).

$^1$H-NMR (δppm in CDCl$_3$): 0.06 (6H, s), 0.09 (9H, s), 0.7–1.0 (12H), 1.12 (3H, s), 1.0–1.5 (6H, m), 2.0–3.6 (11H, m), 3.71 (3H, s), 3.9–4.4 (1H, m), 5.1–5.9 (4H, m), 5.9–6.9 (1H, m).

IR (neat): 3020, 1745, 1645, 1245, 1150, 1100, 1060, 1000, 890, 860, 835, 775, 750 cm$^{-1}$.

EXAMPLE 8

Synthesis of (dl)-(4Z)-15-deoxy-16-methyl-11-t-butyldimethylsilyl-16-trimethylsilyloxy-$\Delta^4$-$^{PGE}$1 methy ester Tetrakis (triphenylphosphine) palladium (0) (52 mg, 0.045 m mol, 3 mol %) was added to (dl)-(4Z)-7,8-dehydro-15-deoxy-16-methyl-11-t-butyldimethylsilyl-16-trimethyl-silyloxy-$\Delta^4$-$PGE_1$ methyl ester (846 mg, 1.50 m mol), to which tributyltin hydride (4.37 g, 15 m mol)

was added with stirring in the atmosphere of nitrogen at room temperature during 3 hours.

Thus resulting reaction mixture was then subjected to column chromatography on silica gel (firstly hexane only, then hexane: ether=10:1) to give (dl)-(4Z)-15-deoxy-16-methyl-11-t-butyldimethylsilyl-16-trimethylsilyloxy-$\Delta^4$-PGE$_1$ methyl ester (610 mg., 1.08 m mol, yield 72%).

Rf=0.40 (hexane: ether=2:1).

$^1$H-NMR ($\delta$ppm in CDCl$_3$): 0.03 (6H, s), 0.10 (9H, s), 0.87 (12H), 1.17 (3H, s), 1.0-1.8 (8H, m), 1.8-3.0 (12H, m), 3.71 (3H, s), 3.8-4.3 (1H, m), 5.1-5.9 (4H, m).

IR (neat): 3000, 1740, 1245, 1150, 1115, 1095, 1000, 970, 860, 835, 775, 750 cm$^{-1}$.

EXAMPLE 9

Synthesis of (dl)-(4Z)-15-deoxy-16-methyl-16-hydroxy-$\Delta^4$-$^{PGE}$1 methyl ester The (dl)-(4Z)-15-deoxy-16-methyl-11-t-butyldimethylsilyl-16-trimethylsilyloxy-$\Delta^4$-PGE$_1$ methyl ester (610 mg, 1.08 m mol) obtained in Example 8 was subjected to a similar desilylation reaction with the use of hydrogen fluoride-pyridine complex in acetonitrile according to Example 5, followed by the same work-up and purification by column chromatography (hexane: ethyl acetate=1:2), to give (dl)-(4Z)-15-deoxy-16-methyl-16-hydroxy-$\Delta^4$-PGE$_1$ methyl ester (337 mg, 0.89 m mol, yield 82%).

Rf=0.20 (hexane: ethyl acetate=1:4), $^1$H-NMR ($\delta$ppm in CDCl$_3$): 0.89 (3H, m), 1.17 (3H, s), 1.2-1.8 (8H, m), 1.8-3.1 (14H, m), 3.71 (3H, s), 3.8-4.5 (1H, m), 5.2-5.9 (4H, m).

IR (neat): 3400, 3000, 1740, 1160, 1075, 1020, 970, 900, 730 cm$^{-1}$.

EXAMPLE 10

Synthesis of (dl)-(4Z)-1-nor-1-acetoxymethyl-7-hydroxy-15-deoxy-16-methyl-16-trimethylsilyloxy-$\Delta^4$-$^{PGE}$1 11-t-butyldimethylsilyl ether An anhydrous ether solution (3 ml) of 510 mg (1.5 m mol) of (dl)-(E)-4-methyl 4-trimethylsilyloxy-1-iodo-1-octene was cooled to −78° C. and 1.5 ml (3 m mol) of 2.0M t-butyllithium was added to the solution in the atmosphere of nitrogen. The mixture was stirred at −78° C. for 1 hour. Then 3 ml of homogeneous anhydrous ether solution of 196 mg (1.5 m mol) of 1-pentynylcopper and 490 mg (3 m mol) of hexamethylphosphorous triamide was added thereto and the mixture was stirred at −78° C. for 1 hour.

Then 2 ml of an anhydrous THF solution of 318 mg (1.5 m mol) of (dl)-4-t-butyldimethylsilyloxy-2-cyclopentenone was added to the mixture and the resulting mixture was stirred at −78° C. for 30 minutes and at −50° C. for additional 40 minutes.

Thereafter, 3 ml of anhydrous ether solution containing 270 mg (1.6 m mol) of (3Z)-7-acetoxy-3-hexenal was added to the preceding solution and was stirred for 1 hour.

The reaction was terminated by use of 2.0M acetate buffer solution and the reaction mixture was extracted with hexane. After having been dried, the organic layer was concentrated and subjected to column chromatography over silica gel (hexane: ethyl acetate=8:1) to afford 644 mg (yield 72%) of the desired (dl)-(4Z)-1-nor-1-acetoxymethyl-7-hydroxy-15-deoxy-16-methyl-16-trimethylsilyloxy-$\Delta^4$-PGE$_1$11-t-butyldimethyl-silyl ether.

$^1$H-NMR ($\delta$ppm in CDCl$_3$): 0.06 (6H, s), 0.10 (9H, s), 0.90 (12H), 1.16 (3H, s), 1.2-1.5 (6H, m), 2.0 (3H, s), 1.9-3.1 (12H, m), 3.2-3.4 (1H, m), 3.7-4.4 (4H, m), 5.15-6.10 (4H, m).

IR (neat, cm$^{-1}$): 3500, 3000, 1740, 1250.

EXAMPLE 11

Synthesis of (dl)-(4Z)-1-nor-1-acetoxymethyl-7,8-dehydro-15-deoxy-16-methyl-16-trimethylsilyloxy-$\Delta^4$-$^{PGE}$1-11-t-butyldimethylsilyl ether In the same way as adopted in Example 7, 540 mg (0.91 m mol) of (dl)-(4Z)-1-nor-1-acetoxymethyl-7-hydroxy-15-deoxy-16-methyl-16-trimethylsilyloxy-$\Delta^4$-PGE$_1$ 11-t-butyldimethylsilyl ether dissolved in 5 mol of a methylene chloride was allowed to react with 305 mg (2.5 m mol) of 4-dimethylaminopyridine and 91 ml (135 gm, 1.1 m mol) of methanesulfonyl chloride. The reaction mixture was subjected to the similar work-up and was purified by column chromatography to yield 394 mg (yield 75%) of (dl)-(4Z)-1-nor-1-acetoxymethyl-7,8-dehydro-15-deoxy-16-methyl-16-trimethylsilyloxy-$\Delta^4$-PGE$_1$11-t-butyldimethylsilyl ether.

$^1$H-NMR ($\delta$ppm in CDCl$_3$): 0.06 (6H, s), 0.09 (9H, s), 0.7-1.0 (12H), 1.12 (3H, s), 1.0-1.5 (6H, m), 2.0 (3H, s), 2.0-3.6 (11H, m), 3.9-4.4 (3H, m), 5.1-5.9 (4H, m), 5.9-5.9 (1H, m).

IR (neat, cm$^{-1}$): 3020, 1745, 1645, 1245.

EXAMPLE 12

Synthesis of (dl)-(4Z)-1-nor-1-acetoxymethyl-15-deoxy-16-methyl-16-trimethylsilyloxy-$\Delta^4$-$^{PGE}$1-11-t-butyldimethylsilyl ether To a solution of 350 mg (0.61 m mol) of (dl)-(4Z)-1-nor-1-acetoxymethyl-7,8-dehydro-15-deoxy-16-methyl-16-trimethylsilyloxy-$\Delta^4$-PGE$_1$ 11-t-butyldimethylsilyl ether obtained in Example 11 in 6 ml of methanol, 1 ml of acetic acid was added.

With stirring, 2 g of zinc dust was added to the mixture and the resulting mixture was stirred at room temperature for 5 hours. The reaction was terminated upon addition of a saturated aqueous solution of sodium hydrogencarbonate and the reaction mixture was extracted with ether. After the organic layer was dried, the solvent was removed by evaporation, and the obtained crude product was subjected to column chromatography over silica gel to give, 212 mg (yield 60%) of (dl)-(4Z)-1-nor-1-acetoxymethyl-15-deoxy-16-methyl-16-trimethylsilyloxy-$\Delta^4$-PGE$_1$-11-t-butyldimethylsilyl ether.

$^1$H-NMR ($\delta$ppm, CDCl$_3$): 0.03 (6H, s), 0.10 (9H, s), 0.87 (12H), 1.17 (3H, s), 1.0-1.8 (8H, m), 2.0 (3H, s), 1.8-3.0 (12H, m), 3.8-4.3 (3H, m), 5.1-5.9 (4H, m), IR (neat, cm$^{-1}$): 3000, 1740, 1245.

EXAMPLE 13

Synthesis of (dl)-(4Z)-1-nor-1-acetoxymethyl-15-deoxy-16-methyl-16-hydroxy-$\Delta^4$-$^{PGE}$1

Two hundred milligrams (0.34 m mol) of (dl)-(4Z)-1-nor-1-acetoxymethyl-15-deoxy-16-methyl-16-trimethylsilyloxy-$\Delta^4$-PGE$_1$ 11-butyldimethylsilyl ether obtained in Example 12 was subjected to the desilylation reaction with the use of hydrogen fluoride-pyridine complex in acetonitrile according to Example 9, followed by the similar work-up and purification by column chromatography (hexane: ethyl acetate=1:2) to give 109 mg (yield 81%) of (dl)-(4Z)-1-nor-1-acetoxymethyl-15-deoxy-16-methyl-16-hydroxy-$\Delta^4$-PGE$_1$.

$^1$H-NMR ($\delta$ppm, CDCl$_3$): 0.90 (3H, m), 1.17 (3H, s), 1.2–1.8 (8H, m), 2.0 (3H, s), 1.8–3.1 (14H, m), 3.8–4.5 (3H, m), 5.2–5.9 (4H, m), IR (neat, cm$^{-1}$): 3400, 300, 1740.

INDUSTRIAL APPLICATIONS

A new process of this invention has made it possible to advantageously produce 16-substituted prostaglandin Es, which are useful as a medicine having an anti-ulcer activity, on an industrial scale. Also 7-hydroxy-16-substituted prostaglandin Es and 16-substituted $\Delta^7$-prostaglandin Es, which are formed as the synthetic intermediates in the aforementioned process, are per se useful compounds as medicine.

What we claim is:

1. A process for producing 16-substituted prostaglandin Es, which include compounds expressed by the following formula (I), or their enantiomers, or their mixtures of arbitrary mixing ratio,

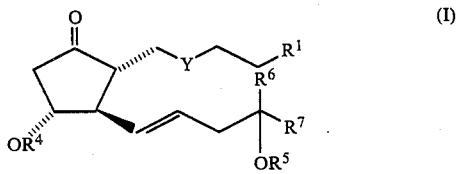
(I)

wherein R$^1$ indicates COOR$^2$, CH$_2$OR$^3$, in which R$^2$ indicates a hydrogen atom, a substituted or unsubstituted C$_1$–C$_{10}$ alkyl group, a substituted or unsubstituted C$_3$–C$_{10}$ cycloalkyl group, or a substituted or unsubstituted phenyl group, and R$^3$ indicates a hydrogen atom, a tri(C$_1$–C$_7$) hydrocarbon silyl group, a group which forms an acetal bond together with the oxygen atom of a hydroxyl group, or a C$_2$–C$_7$ aryl group: R$^4$ and R$^5$ are identical or different, each representing a hydrogen atom, a tri(C$_1$–C$_7$) hydrocarbon silyl group, or a group which forms an acetal bond together with the oxygen atom of a hydroxyl group; R$^6$ indicates a hydrogen atom, a C$_1$–C$_4$ alkyl group, or vinyl group; R$^7$ indicates a linear or branched C$_3$–C$_8$ alkyl group, an alkenyl group, or an alkynyl group, which may contain an oxygen atom; a phenyl group, a phenoxy group, or a C$_3$–C$_{10}$ cycloalkyl group, which may be substituted; or a linear or branched C$_1$–C$_5$ alkyl group which is substituted by a C$_1$–C$_6$ alkoxy group, a phenyl group, a phenoxy group, or a C$_3$–C$_{10}$ cycloalkyl group, which may be substituted; and Y indicates CH$_2$X or XCH$_2$, in which X represents an ethylene group, a cis- or trans-vinylene group, or an ethynylene group, which process comprises selectively reducing using an organic tin hydride compound and a zerovalent palladium catalyst the double bonds at the 7- and 8-positions of 16-substituted $\Delta^7$-prostaglandin Es, which include compounds expressed by the following formula (II), their enantiomers, or their mixtures of arbitrary mixing ratio, further followed by the deprotecting reaction and/or the hydrolytic reaction, if necessary,

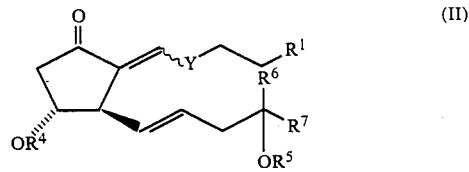
(II)

wherein R$^1$, R$^4$, R$^5$, R$^6$, R$^7$, and Y are as defined hereinabove.

* * * * *